US011963739B2

(12) United States Patent
Goertzen et al.

(10) Patent No.: US 11,963,739 B2
(45) Date of Patent: Apr. 23, 2024

(54) BRAINPET SYSTEM FOR SIMULTANEOUS MRI AND PET IMAGING

(71) Applicant: Sino Canada Health Institute Inc., Winnipeg (CA)

(72) Inventors: Andrew Goertzen, Winnipeg (CA); John Saunders, Winnipeg (CA); James Schellenberg, Winnipeg (CA); Ryan Sparkes, Winnipeg (CA); Gong Zhang, Winnipeg (CA)

(73) Assignee: Sino Canada Health Engineering Research Institute (Hefei) Ltd, Hefei (CN)

( * ) Notice: Subject to any disclaimer, the term of this patent is extended or adjusted under 35 U.S.C. 154(b) by 0 days.

(21) Appl. No.: 17/429,179

(22) PCT Filed: Nov. 13, 2020

(86) PCT No.: PCT/CA2020/051548
§ 371 (c)(1),
(2) Date: Aug. 6, 2021

(87) PCT Pub. No.: WO2021/092693
PCT Pub. Date: May 20, 2021

(65) Prior Publication Data
US 2022/0280041 A1      Sep. 8, 2022

Related U.S. Application Data

(60) Provisional application No. 62/934,653, filed on Nov. 13, 2019.

(51) Int. Cl.
*A61B 5/00* (2006.01)
*A61B 5/055* (2006.01)
(Continued)

(52) U.S. Cl.
CPC .......... *A61B 5/0035* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 7,286,867 B2   10/2007   Schlyer et al.
8,401,613 B2    3/2013   Choi et al.
(Continued)

OTHER PUBLICATIONS

Schlemmer et al. "Simultaneous MR/PET Imaging of the Human Brain: Feasibility Study", Radiology, vol. 248, No. 3, pp. 1028-1035, Sep. 2008.
(Continued)

*Primary Examiner* — Rodney E Fuller
(74) *Attorney, Agent, or Firm* — Michael R. Williams; Ryan W Dupuis; Ade & Company Inc.

(57) ABSTRACT

In order to improve both spatial resolution and sensitivity for brain research and clinical activity, we have designed a combined PET/MRI insert for brain scanning, referred to herein as a "BrainPET insert" that can be fit onto and into a suitable MRI system. The BrainPET Insert comprises, in order, a receive (Rx) coil positioned within and adjacent to a transmit (Tx) coil and a PET ring, wherein both the Rx coil and the Tx coil are within the PET ring.

12 Claims, 6 Drawing Sheets

(51) Int. Cl.
  *A61B 6/00* (2006.01)
  *A61B 6/03* (2006.01)
  *A61B 6/04* (2006.01)
  *A61B 6/50* (2024.01)
  *G01R 33/48* (2006.01)
(52) U.S. Cl.
  CPC .............. *A61B 5/704* (2013.01); *A61B 6/037* (2013.01); *A61B 6/0407* (2013.01); *A61B 6/501* (2013.01); *A61B 6/5247* (2013.01); *G01R 33/4806* (2013.01)

(56) References Cited

U.S. PATENT DOCUMENTS

| | | | |
|---|---|---|---|
| 8,525,116 B2* | 9/2013 | Schulz | G01T 1/1603 600/407 |
| 9,591,989 B2 | 3/2017 | Tai | |
| 10,080,534 B2* | 9/2018 | Yamagata | A61B 5/055 |
| 10,114,086 B2* | 10/2018 | Gagnon | G01R 33/421 |
| 2008/0260104 A1* | 10/2008 | Schmidt | A61B 6/5247 378/198 |
| 2011/0224534 A1 | 9/2011 | Yamaya et al. | |
| 2012/0136237 A1* | 5/2012 | Benlloch Baviera | H01L 27/14627 600/411 |
| 2012/0330128 A1* | 12/2012 | Park | A61B 6/4275 600/411 |
| 2013/0030287 A1 | 1/2013 | Yamaya | |
| 2013/0234710 A1* | 9/2013 | Kanno | A61B 5/0035 324/318 |
| 2014/0275965 A1* | 9/2014 | Majewski | A61B 6/501 600/411 |
| 2017/0164915 A1 | 6/2017 | Li et al. | |
| 2018/0252785 A1* | 9/2018 | Glowacz | G01T 1/1603 |

OTHER PUBLICATIONS

Stefaan Vandenberghe et al: "PET-MRI: a review of challenges and solutions in the development of integrated multimodality imaging", Physics in Medicine and Biology, Institute of Physics Publishing, Bristol GB, vol. 60, No. 4, Feb. 4, 2015 (Feb. 4, 2015), XP020278946, ISSN: 0031-9155, DOI: 10.1088/0031-9155/60/4/R115 [retrieved on Feb. 4, 2015].

Belcari Nicola et al: "Design and Detector Performance of the PET Component of the Trimage PET/MR/EEG Scanner", IEEE Transactions On Radiation and Plasma Medical Sciences, IEEE, vol. 3, No. 3, May 1, 2019 (May 1, 2019), pp. 292-301, XP011722689, ISSN: 2469-7311, DOI: 10.1109/TRPMS.2019.2906407.

* cited by examiner

BRAINPET SYSTEM FOR SIMULTANEOUS MRI AND PET IMAGING

PRIOR APPLICATION INFORMATION

The instant application is a 371 of PCT Application PCT/CA2020/051548, filed Nov. 13, 2020, which claimed the benefit of U.S. Provisional Application Ser. No. 62/934,653, now abandoned, filed Nov. 13, 2019 and entitled "BrainPET System for Simultaneous MRI and PET Imaging", the entire contents of which are incorporated herein by reference for all purposes.

BACKGROUND OF THE INVENTION

Simultaneous imaging of the human brain using PET and MRI modalities is an advanced imaging method for improved spatial resolution, sensitivity, and accuracy—both for anatomy and for metabolic activity. Simultaneous imaging refers to imaging that is done at the same time and on the same body volume.

For brain imaging, it is believed that important research and clinical applications can be done using a simultaneous PET-MRI imaging system. It is believed that neurodegenerative diseases such as Alzheimer's and Parkinson's, brain cancer diagnosis, treatment monitoring, and staging, and epilepsy surgery planning and assessment are all medical areas that can benefit from the MRI+PET combined system.

The Siemens Biograph mMR system and General Electric Signa are two existing examples of such a system, and both feature an integrated large-bore PET inside the MRI. The two subsystems, PET and MRI, are built together into one integrated system. In these systems, the PET inner diameter is approximately 60 cm. The brain imaging capability that can be achieved with these systems include a spatial resolution of approximately 2 to 4 mm. For this integrated system design, the PET and MRI are built together and cannot be separated at the customer site.

This simultaneous imaging creates two data sets: an MRI dataset and a PET dataset. In general, different imaging modalities have different voxel sizes and different equipment orientations, so spatial alignment (called registration) of these different datasets needs to be done in order to properly overlay the image results from one modality to the other.

Whereas the integrated PET-MRI systems from Siemens or GE are useful for those sites that have not already purchased an MRI, it would be useful to have a PET+MRI simultaneous imaging system which can be retrofit to already installed MRI systems. In this case, the PET system would not be integrated with the MRI but would fit inside the MRI either in a permanent or removable fashion. For these types of retrofit systems, it is possible to build a PET system with a smaller inner bore size for a specific application like brain imaging.

For both retrofit and integrated systems, electronic data acquisition systems are used to convert the analog output of the PET pixels into digital outputs. A key design decision for simultaneous PET+MRI systems is the amount of electronics that will be positioned inside the MRI field. For example, these electronics may amplify the signals coming from the PET detectors, may provide shaping of the signals from the PET detectors, and may convert the analog signals from the PET detectors into digital signals suitable for image processing. These electronics typically generate heat, and therefore cooling inside the MRI bore is often needed if the electronics are placed inside the MRI bore. In addition, the electronics often create additional electromagnetic noise that can interfere with the MRI imaging system, and so additional EM (electromagnetic) shielding may be required. In addition, placing the electronics in the MRI bore requires additional space within the MRI, leading to a reduction in the bore diameter available for the patient. For example, in the Siemens Biograph mMR PET/MRI system, the MRI bore is 70 cm but the inclusion of the PET system reduces the bore to 60 cm. In addition, the MRI operation during transmit and receive may create additional electronic noise for the PET imaging system.

An alternative method of positioning the electronics is to place less electronics in the MRI bore and to transmit the PET detector signals out of the bore using cables to an MR-Safe or MR-Compatible equipment rack beside the MRI that can perform the electronics function(s). A system like this will usually have an electronics rack that can operate properly in the fringe field of the MRI, and which can use a suitable cooling system such as air fans, with the fans allowing for successful cooling of the electronics that are outside the MRI bore. In this type of design, cooling of the electronics inside the MRI bore is often not required.

Publications and Prototypes that discuss and explore the combination of PET and MRI have been occurring since 1995.

Publications from the group of Simon Cherry describing combining PET and MRI include: "Simultaneous PET and MR imaging", Y. Shao et al, Phys. Med. Biol. October 1997 42(10), 1965-70; "Contemporaneous positron emission tomography and MR imaging at 1.5T", K. Farahani et al, J. Magn. Res. Imaging March 1999, 9(3):497-500; "A study of artefacts in simultaneous PET and MR imaging using a prototype MR compatible PET scanner", R B Slates et al, Phys. Med. Biol. August 1999; 44 (8):2015-27.

U.S. Pat. No. 5,719,400 (Cherry) issued Feb. 17, 1998 disclosed a high-resolution detector for use in PET scanning which is suitable for use in combined PET/MRI systems.

"Simultaneous PET and NMR", The British Journal of Radiology, 75(2002), S53-S59 describes a small prototype PET scanner that is MR compatible. In this case, four meter sections of optical fiber are used to transport the scintillation signals to photomultiplier tubes that are removed from the high magnetic field area of the bore. They discuss the potential advantages for both temporal and spatial correlation. As they indicate in this paper, "incorporation of PET and MR scanners into a single gantry would keep subject motion and tissue deformation between PET and MR acquisitions to an absolute minimum, as is the approach adopted for the combined PET and CT systems described elsewhere in this special issue (their references 2, 3)"

"Whole-Body Imaging with PET/MRI", European Journal of Medical Research, Jun. 30, 2004, page 309-312, states, regarding the combination of PET and MRI into a single scanner, "The combination of these two excellent diagnostic imaging modalities into a single scanner offers several advantages in comparison to PET and MRI alone".

U.S. Pat. No. 6,946,841 (Rubashov) issued Sep. 20, 2005 disclosed a combination NMR/PET scanner for breast tissue where the PET scanner ring is mounted outside the magnet bore and the patient is moved between the two scanning positions.

An additional publication is "MR-PET: Combining Function, Anatomy and More", M. Schwaiger et al, September 2005 Medical Solutions, pp. 25-30. This publication provides a simple diagram which shows a Siemens Magnetom Espree with a modified bore liner assembly. In this bore liner assembly is shown an RF body coil, above which is the PET camera elements. The diagram indicates that PET is acquired with a ring inserted into the magnet—simultaneous acquisitions are possible. In this case, the scintillation detectors are using APD (Avalanche PhotoDiodes) photosensors, which is the type of design that Siemens used in their Biograph mMR.

The article "The New Challenges of Brain PET Imaging Technology", published in Current Medical Imaging Reviews, 2006, 2, 3-13, by Habib Zaidi and Marie-Louise Montandon, demonstrates through a prototype construction that combined PET/MRI scanners are possible.

An early discussion of the integration of SiPM (Silicon PhotoMultiplier) PET and MRI devices can be found in the papers listed here: Hawkes, R., A. Lucas, J. Stevick, G. Llosa, S. Marcatili, C. Piemonte, A. Del Guerra and T. A. Carpenter (2007). *Silicon photomultiplier performance tests in magnetic resonance pulsed fields*. Nuclear Science Symposium Conference Record, 2007. NSS '07. IEEE.

Spanoudaki, V. C. and et al. (2007). "Use of single photon counting detector arrays in combined PET/MR: Characterization of LYSO-SiPM detector modules and comparison with a LSO-APD detector." *Journal of Instrumentation* 2(12): P12002.

In addition, an early patent from SensL U.S. Pat. No. 8,669,513 which was filed in 2007 discussed the SiPM design and mentions that integration with MRI is of interest.

One patent granted in 2013 that discusses some of these issues is Choi et al, U.S. Pat. No. 8,401,613 called PET-MRI Combination Apparatus. In this patent the signal is cabled out of the MRI bore to electronics outside the bore. The electronics outside of the bore include signal amplification, which includes a preamplifier and a shaping amplifier, and a signal processing circuit. In this case, the cabling connects to the photosensor being used, which is a direct form of readout. For the discussion presented herein, we use a four-corner readout architecture, in which the cabling is not directly connected to the photosensor. In this patent, the discussion was centered around one output signal per photosensor, whereas there are alternative readout designs that include both energy and timing considerations, as discussed below.

U.S. Pat. No. 9,880,236 from Toshiba discusses a PET-MRI combination apparatus.

U.S. Pat. No. 9,737,274 from Mediso discusses a PET ring used for brain imaging of a human or primate.

US Patent Application 20170164915 from United Imaging discusses PET-MRI apparatus.

US Patent Application 20140275965 from Majewski et al discusses the combination of PET and MRI devices.

SUMMARY OF THE INVENTION

According to a first aspect of the invention, there is provided a BrainPET System comprising a BrainPET Insert, a BrainPET cart and a BrainPET workstation with appropriate acquisition and reconstruction software. Copper cabling connects the Insert and the Cart. Fiber cabling connects the Cart and the Workstation. The Insert is used inside the MRI Bore, the Cart is positioned inside the MRI Room and the Workstation is positioned inside the MRI Control Room or in an equipment area outside of the MRI Room.

The BrainPET Insert comprising, in order, a receive (Rx) coil positioned within and adjacent to a transmit (Tx) coil and a PET ring, wherein both the Rx coil and the Tx coil are within the PET ring.

Preferably, the BrainPET insert is for use in brain imaging, specifically, simultaneous MRI and PET brain imaging.

According to another aspect of the invention, there is provided a method of simultaneous PET and MRI imaging of a patient's brain in an MRI system comprising a front, a back, a bore, a control system and a patient bed, said method comprising:

providing a BrainPET Insert comprising, in order, a receive (Rx) coil positioned within and adjacent to a transmit (Tx) coil and a PET ring, wherein both the Rx coil and the Tx coil are within the PET ring, said patient bed comprising a sliding system extending from a position outside of the bore to a position within the bore, said sliding system moving the BrainPET insert from a first position wherein the BrainPET insert is mounted on the sliding system outside of the bore and a second position wherein the BrainPET insert is within the bore;

moving the patient bed out of the back of the MRI device, thereby exposing a loading portion of the patient bed;

mounting the BrainPET Insert onto the loading portion of the patient bed such that the BrainPET insert is mounted on the sliding system and in the first position;

moving the patient bed out of the front of the MRI device for patient loading;

loading a patient onto the patient bed;

moving the patient bed such that the patient is moved into the bore;

moving the BrainPET insert from the first position to the second position such that the BrainPET insert is positioned around the head of the patient; and generating MRI and PET scans of the brain of the patient.

As discussed below, in some embodiments, the patient places their head on a head holder. When the patient is in position and the imaging is about to start, the nurse or technician can move the BrainPET insert forward into the imaging position.

According to another aspect of the invention, there is provided a BrainPET Insert comprising, in order, a receive (Rx) coil positioned within and adjacent to a transmit (Tx) coil and a PET ring, wherein both the Rx coil and the Tx coil are within the PET ring.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

In order to improve both spatial resolution and sensitivity for brain research and clinical activity, we have designed a combined PET/MRI insert for brain scanning, referred to herein as a "BrainPET insert" that can be fit onto and into a suitable MRI system. In the examples, the retrofitting of a Siemens Biograph mMR system is described; however, as will be apparent to one of skill in the art, the PET insert can be used with other suitable MRI devices including for example whole body PET/MRI systems. The design of such a PET insert is discussed herein.

Published PCT Application WO06/071922 discloses the Avalanche Photodiode (APD) for use in simultaneous PET/MRI imaging configured in which a pre-amplifier is located within the MRI bore.

U.S. Pat. No. 8,401,613 teaches a PET detector installed within imaging space of the MRI bore with a PET circuit unit installed outside of the bore to prevent the PET circuit unit from being influenced by the magnetic field in the MRI bore.

Specifically, this patent teaches inserting the PET scanner within the MRI bore so as to minimize problems with alignment of the MRI and PET scans.

While this arrangement allows for simultaneous imaging of the brain with MRI and PET scanners, constant exposure of the PET scanner to the magnetic field generated by the MRI bore may reduce the functionality of the PET scanner. In addition, if a PET insert is permanently attached in a position on the patient bed, then the MRI scanner is converted into a head only PET/MRI scanner, which will limit the utility of the MRI scanner for, for example, a hospital.

Referring to the Figures, described herein is a BrainPET Insert 11 that can be attached onto the patient bed 16 when imaging is required, and which can also be lifted and removed off of the patient bed 16 when MRI only imaging is desired. By removing the PET Insert 11 when not in use, the MRI scanner 13 (referred to alternatively as "MRI scanner", "MRI bore" or "MRI") can be used for only MRI activity and the PET Insert is not unnecessarily damaged by the MRI fields.

Specifically, when MRI only imaging is desired the BrainPET Insert 11 is housed on the cart 12 and the cart 12 can be moved away from the rear of the MRI bore 13. In this position the BrainPET Insert 11 is outside of and exterior to the magnetic bore of the MRI 13 and can be positioned in the room to minimize the exposure to the full strength of the MRI field.

Figure 1:
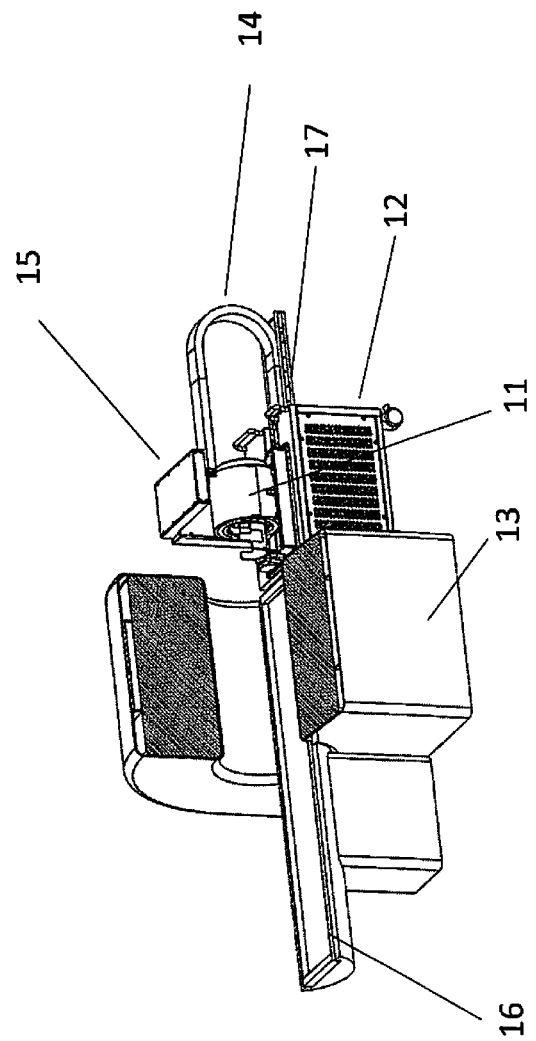
FIG. 1 is a schematic drawing showing the BrainPET scanner at the back of the device.
Figure 2:
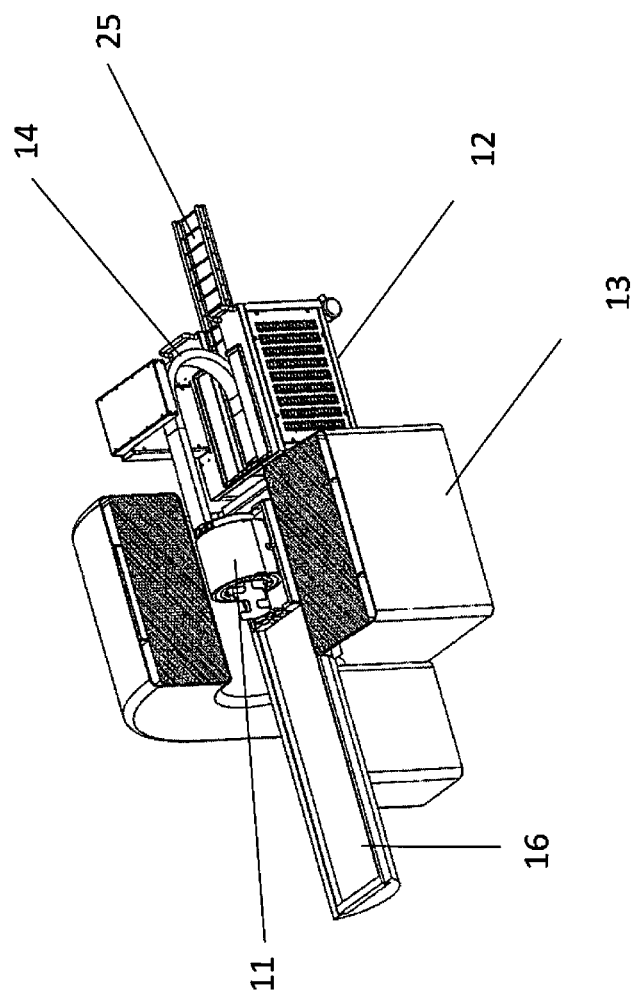
FIG. 2 is a schematic drawing showing the BrainPET scanner extended into the magnetic bore.

When PET/MRI imaging is desired, the BrainPET Insert 11 can be loaded onto the patient bed 16 using the procedure as described below and as shown in FIGS. 1 and 2.

Specifically, FIG. 1 is a schematic drawing of the BrainPET system showing the BrainPET scanner 11 and cart 12 at the back of the MRI 13. The BrainPET scanner 11 is connected to the cart 12 by a copper cable 14 and cable management system 17, with this copper cable 14 may have a length of 10 to 20 feet, depending on the type of MRI 13 that is being used. The BrainPET scanner 11 (also referred to herein as the BrainPET insert 11) may weighs between 50 and 100 pounds, and so a scanner movement system 15 is required to lift the BrainPET scanner 11 and place it on the MRI patient bed 16. This figure shows a cart 12, MRI 13, BrainPET scanner 11 and cable management system. The BrainPET workstation and fiber connection to the workstation are not shown.

Specifically, when the patient is not yet on the bed or the BrainPET scanner 11 is not being used, the BrainPET scanner 11 is in the back position or loading position. While in the back position, the BrainPET scanner 11 is outside of and exterior to the magnetic bore of the MRI 13. One example of this arrangement is shown in FIG. 1, which shows the patient bed 16 as extended for supporting the BrainPET scanner 11 when in the back position.

FIG. 2 is a schematic drawing showing the BrainPET Scanner 11 extended into the MRI bore 13. This figure shows the cart 12 at the back of the MRI 13, with the copper cable 14 extending into the MRI bore. The cable management tray 25 is used to hold the copper cable 14 when it is not extended into the MRI bore 13. When the copper cable 14 is inside the MRI 13, the cable management tray 25 may be folded into the cart 12 or may remain extended from the cart 12, depending on the details of the design.

Thus, in these embodiments, the BrainPET scanner 11 is arranged to be moved between two positions: a forward or imaging position (shown in FIG. 2) wherein the BrainPET scanner 11 is within the MRI bore 13 and a back or loading position (shown in FIG. 1) wherein the BrainPET scanner 11 is outside of the MRI bore 13.

The BrainPET insert 11 is shown in FIGS. 3, 5, 6 and 7.

Specifically, FIG. 1 is a BrainPET Insert 11 rendering showing Headholder 31, PET Ring 32, and Tx/Rx coil 33. The PET Ring 32 and Tx/Rx coil 33 are connected together into a single moveable unit, and they slide forwards and back on the Slide Platform 34, as discussed below. There are two locking positions for the PET Ring 32 and Tx/Rx coil 33, with the back or front position both being locked in place using locks 35 on the side of the PET Ring 32. Only one lock 35 is shown in this view.

Figure 8:
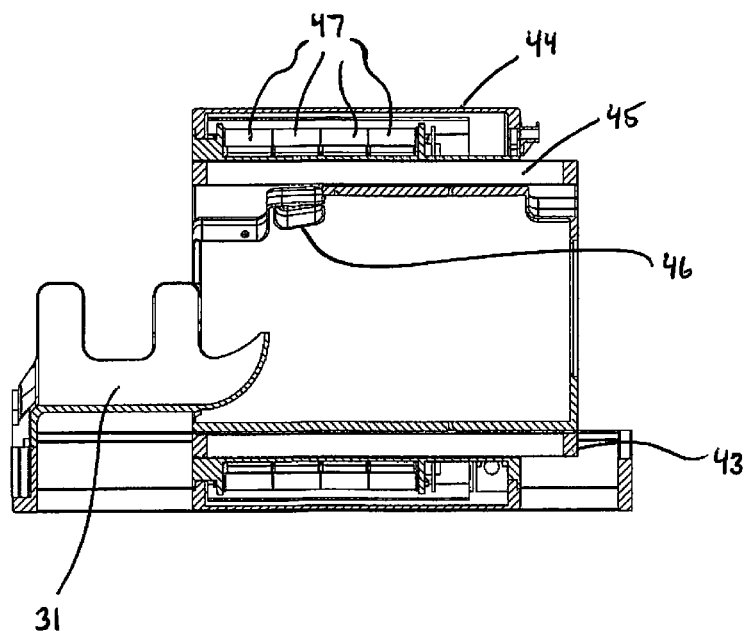
FIG. 8 is a side view in cross section along line A-A of FIG. 7 of the BrainPET insert.
Figure 9:
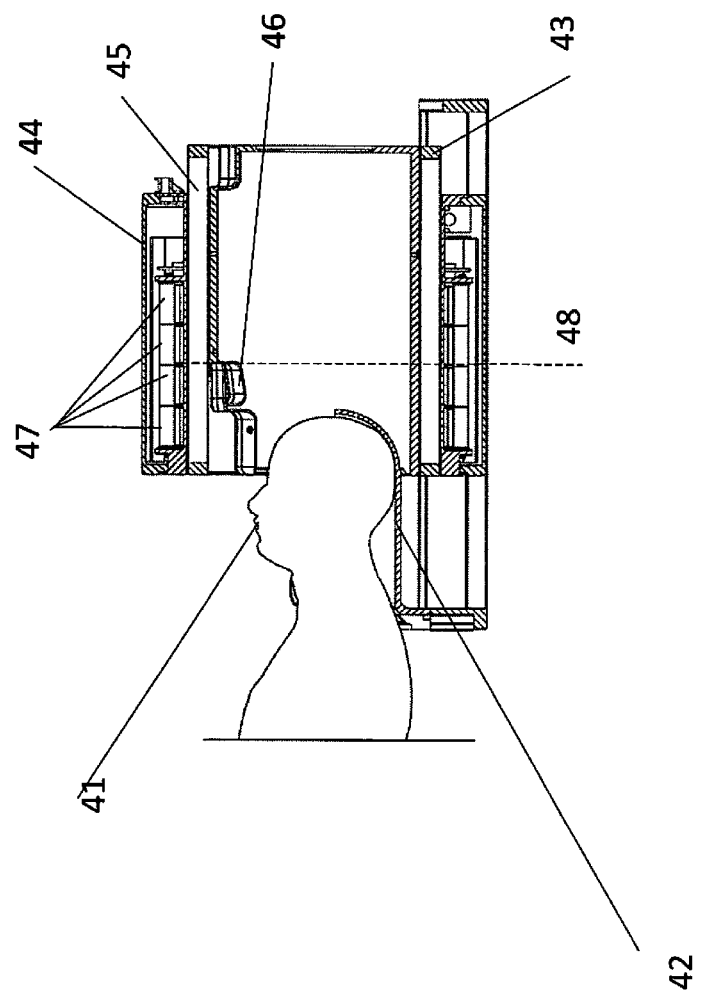
FIG. 9. A schematic drawing from a side view in cross section along line A-A of FIG. 7, showing the patient's head positioned in the BrainPET scanner.

As can be seen in FIGS. 8 and 9, The Rx coil 46 is at the inner-most position within the insert; the Tx coil 45 is outside of and adjacent to the Rx coil 46 and both the Rx coil 46 and the Tx coil 45 are within the PET ring 32.

Specifically, FIG. 9 is a side view schematic drawing showing the patient's head 41 positioned on the headholder 31, with the BrainPET scanner 11 not fully over the patient's head 41. The BrainPET Scanner consists of PET Ring 32, inside of which is the Tx coil 45, inside of which is the Rx coil 46. Inside the PET ring 32 are positioned the 4 scintillator blocks 47. The axial positioning of these scintillator blocks 47 identify the PET Center of the field of view 48. The design of the system allows the PET isocenter to be positioned in line with the MRI isocenter. One method of aligning these two isocenters is to place a mark on the outside top of the PET Ring, and then using the Siemens alignment laser to accurately mark and move the patient to the middle of the MRI bore 13, as discussed below.

As can be seen therein, the Tx coil 45 and the Rx coil 46 are positioned within the PET ring 31, as discussed below. As discussed herein, the BrainPET insert 11 is arranged such that the Txcoil 45 and the Rx coil 46 and the individual circuit boards of the PET ring 31 can be removed from the BrainPET insert 11. As will be appreciated by one of skill in the art, this facilitates the use of phantoms for calibrating the Tx coil 45, the Rx coil 46 and/or the PET ring 32.

Figure 4:
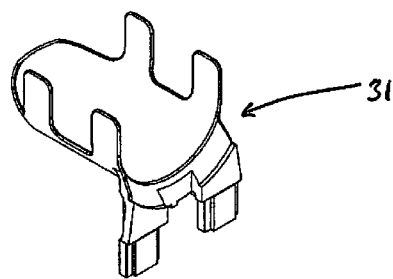
FIG. 4 is a perspective view of the headholder.

FIG. 4 is a perspective view of the headholder 31. As discussed herein, in some embodiments, the headholder is placed on the patient bed 16 for supporting the patient's head and in use, the patient's head is inserted into the headholder 31 and the BrainPET insert 11 is then moved from the back position to the forward position such that the headholder 31 and the patient's head 41 are within the BrainPET insert 11.

Figure 5:
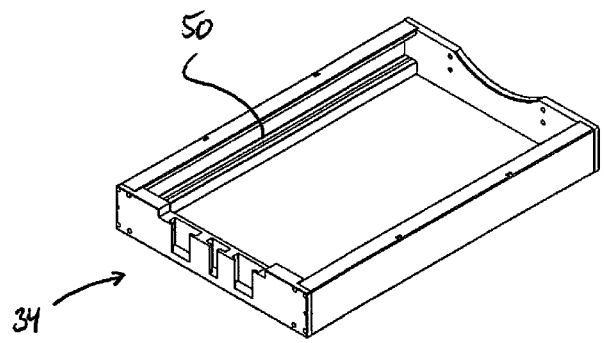
FIG. 5 is a perspective view of the slide platform.

FIG. 5 is a perspective view of the slide platform 34 which shows rods 50 extending along the lengthwise sides of the slide platform.

Figure 6:
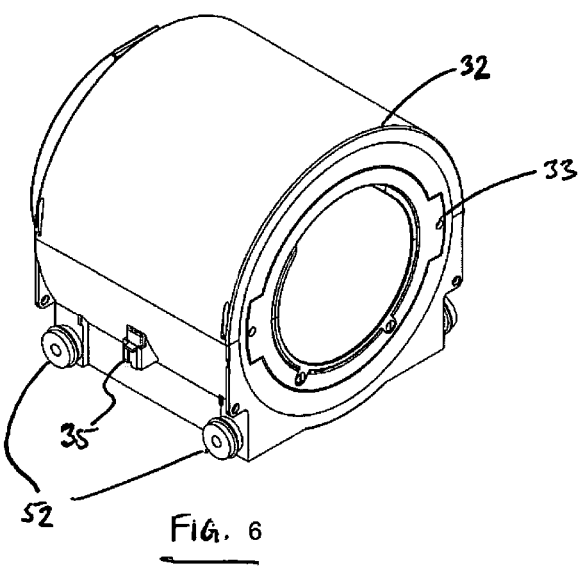
FIG. 6 is a perspective view of the PET Ring and the Tx/Rx coil.
Figure 7:
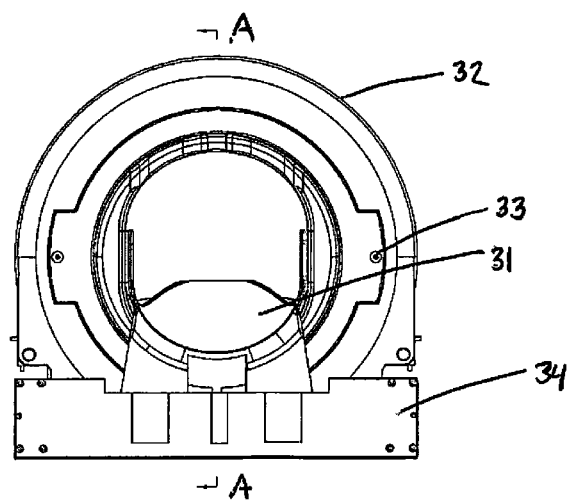
FIG. 7 is a front view of the BrainPET insert.

FIG. 6 is a perspective view of the PET ring 32 and Tx/Rx coil 33 which shows the wheels 52 which roll on the rods 50 of the slide platform 34 when the BrainPET insert 11 is being moved from the back position to the front position, as discussed herein.

As discussed herein, the BrainPET Insert 11 comprises:
a headholder 31,
a PET Ring 32,
a Tx/Rx coil 33, and
a sliding system that allows the PET ring 32 and Tx/Rx coil 33 to slide between the forward or imaging position within the MRI bore 13 and proximal to the patient head when in use and the back or loading position where the BrainPET insert 11 is outside of the MRI bore 13. The purpose of the sliding system is to allow for easy patient positioning. In the back position, the PET ring 32 and Tx/Rx coil 33 is moved away from the headholder 31 so that the patient's head 41 can be easily placed in the headholder 31 and positioned by the attending nurse. The PET ring 32 and Tx/Rx coil 33 can then be slid forward over the patient's head 41 into imaging position. After this movement, the entire patient bed 16 is moved into the MRI bore 13.

In some embodiments, the sliding system comprises a slide platform 34, as discussed above which comprises rods 50 on which wheels 52 attached to the PET Ring 32 and Tx/Rx coil 33 roll. As will be appreciated by one of skill in the art, other suitable sliding systems will be apparent to one of skill in the art and are within the scope of the invention.

As discussed herein, the headholder 31 is arranged to cradle and/or support the head of the patient during imaging.

In some embodiments, the BrainPET insert system is provided with a workstation control system that is arranged to be placed outside of the magnetic field of the MRI bore 13. This workstation control system may include at least an acquisition server function and an image reconstruction function.

Alternatively, in some embodiments, the BrainPET insert system may interact with the control system for the existing MRI system, which may be a PET/MRI system.

In some embodiments, the BrainPET insert system further comprises or includes temperature sensing means for measuring the internal temperature of the BrainPET insert. In these embodiments, the temperature of the insert is monitored in order to adjust the calibration tables or bias voltage to effect insert functionality and/or performance.

In some embodiments, the BrainPET insert is connected to a cart by a copper cable. Preferably, the cart that is located outside of the MRI bore and inside the MRI room, close to the back of the MRI.

As discussed below, in some embodiments, the copper cable comprises a fast signal cable and a slow signal cable.

In some embodiments, the cart is connected to the control unit by a fiber connection, through the waveguide of the RF filter panel.

The control unit may comprise means for connecting to the PACS system or Hospital Network.

In some embodiments, there is also provided a mattress for the patient to place their head beneath the head holder.

In one embodiment of the invention, there is provided a BrainPET Insert comprising, in order, a receive (Rx) coil positioned within and adjacent to a transmit (Tx) coil and a PET ring, wherein both the Rx coil and the Tx coil are within the PET ring.

Preferably, the BrainPET insert is for use in brain imaging, specifically, simultaneous MRI and PET brain imaging.

As will be appreciated by one of skill in the art, the Tx and Rx coil may include cabling and connectors suitable for connecting to an existing MRI such as a Siemens Biograph mMR MRI.

According to another aspect of the invention, there is provided a method of simultaneous PET and MRI imaging of a patient's brain in an MRI system comprising a front, a back, a bore, a control system and a patient bed, said method comprising:

providing a BrainPET Insert comprising, in order, a receive (Rx) coil positioned within and adjacent to a transmit (Tx) coil and a PET ring, wherein both the Rx coil and the Tx coil are within the PET ring, said patient bed comprising a sliding system extending from a position outside of the bore to a position within the bore, said sliding system moving the BrainPET insert from a first position wherein the BrainPET insert is mounted on the sliding system outside of the bore and a second position wherein the BrainPET insert is within the bore;

moving the patient bed out of the back of the MRI device, thereby exposing a loading portion of the patient bed;

mounting the BrainPET Insert onto the loading portion of the patient bed such that the BrainPET insert is mounted on the sliding system and in the first position;

moving the patient bed out of the front of the MRI device for patient loading;

loading a patient onto the patient bed;

moving the patient bed such that the patient is moved into the bore;

moving the BrainPET insert from the first position to the second position such that the BrainPET insert is positioned around the head of the patient; and generating MRI and PET scans of the brain of the patient.

As discussed below, in some embodiments, the patient places their head on a head holder. When the patient is in position and the imaging is about to start, the nurse or technician can move the BrainPET insert forward into the imaging position. As discussed herein, once the BrainPET is in the imaging position, PET and MRI imaging of the patient's brain can take place.

By extending the patient bed out of the back of the MRI, this allows a BrainPET insert to be positioned on the patient bed without the patient being in the room, and then the patient bed can be moved by the MRI to the front of the MRI to allow the patient to get on the bed. Once the patient is on the bed, the BrainPET insert can be moved to the forward or imaging position.

In some embodiments, the BrainPET/MRI insert system further comprises at least one of the following features:

The table on which the patient is placed for imaging, for example, the Biograph table, is extended out past the back of the MRI so that the BrainPET system can be loaded onto the bed. For example, this extension may support the sliding system for moving the BrainPET insert from the loading position to the imaging position. In some embodiments, as discussed above, the sliding system comprises rails which may be extended out past the MRI bore.

In these embodiments, there may also be provided a levered arm or robotic arm or articulated arm that is arranged for lifting the BrainPET Insert onto and off of the patient table. As will be appreciated by one of skill in the art, the BrainPET Insert can be up to 100 pounds or more in weight; as a result of the arrangement, a nurse or technician is not required to lift such a heavy object and can instead rely on the automated method.

The system is arranged such that the signal(s) from the photosensor can be separated into timing and energy outputs in the BrainPET insert and then transmitted outside the MRI for analysis. For example, by using different cabling for the energy and timing signals, important aspects of the signals can be preserved. Specifically, timing signals have a sharp edge to obtain timing information, whereas for energy, it is a smoothed and monotonic amplitude measurement.

As discussed above, in some embodiments, the cable comprises a fast signal cable and a slow signal cable wherein the fast signal cable reports on the start of a scintillation event for use in timing of the event and the slow signal cable reports on the energy of the event. Such a reporting system and the advantages thereof are described in co-pending, co-owned U.S. Provisional Patent Application Ser. No. 62/904,247, filed Sep. 23, 2019 and entitled "Readout Board Interblock Muxing for PET Systems", the entire contents of which are incorporated herein for all purposes but in particular for the teaching of analysis of fast and slow signals. As will be appreciated by one of skill in the art, this represents two different types of cables present in one bundle.

In some embodiments, the copper cabling from the BrainPET insert to the control system, for example, to the rack, is managed through a cable management system, as discussed herein.

In these embodiments, the fast signal cables may comprise a comparator circuit that converts analog signals into digital signals.

Specifically, in these embodiments, the fast signal cables may terminate on a comparator circuit in the BrainPET Insert, with the comparator circuit providing digital output of the fast signal. Terminating the fast signal in the BrainPET Insert, instead of allowing the fast signal to exit the Insert in analog mode, allows sharper edges to be used for timing, thereby improving accuracy and sensitivity of the device.

The system may be arranged such that a portion of the electronics functions are maintained outside of the MRI magnetic field. For example, these functions may include but are by no means limited to SiPM bias voltage control using detector gain control and stabilization algorithms; ADC analog to digital conversion functions for the energy chain of the system; timing functionality in which event timing is determined; and monitoring and measurement in which status monitoring of the BrainPET is provided.

Preferably, SiPM pixels are used as photosensors to minimize the heating load of the separation of the outputs of the fast timing channel pre-amplifier on PET insert.

In some embodiments of the invention, the BrainPET is arranged to slide and to be retractable so that the BrainPET insert and the coil system can be moved back to allow patient to place head in the headholder;

In some embodiments, the headholder is arranged to be removable, to allow for calibration phantoms to be inserted from the front of the insert.

In some embodiments, the Tx/Rx coil is arranged to be removed from the BrainPET insert to allow a calibration phantom to be placed in the PET Ring without having coil obstruction in the way.

In some embodiments, the BrainPET Insert includes locking means for securing the BrainPET in a specific position on the sliding system. As will be appreciated by one of skill in the art, there are many suitable means known in the art for locking a device in a specific location. For example, during imaging, the exact location of the BrainPET relative to the components used for MRI imaging is often critical and as such equipping the patient table and the BrainPET insert with interacting for example interlocking elements such that the BrainPET insert can be physically aligned with the patient table are provided. For example, this may constitute a locking method for the BrainPET insert and coil system, which allows for two or more positions, with the rear position allowing the patient to easily place their head in the headholder, and a front position which accurately positions the eye pieces or eye slots of the coil over the eye locations of the patient and then locks the BrainPET insert in position for imaging, thereby facilitating alignment of the MRI and PET images. As will be appreciated by one of skill in the art, these eye slots are typically used for the orientation of all patients, although this does not take into account differences in head size and/or shape.

The use of the invention is also illustrated in Figures.

In FIG. 1 is a drawing of the BrainPET system showing the BrainPET insert 11 and cart 12 at the back of the MRI 13. The insert 11 is connected to the cart 12 by a copper cable 14 which lies on a cable management system 17, with this copper cable having length 10 to 20 feet depending on the type of MRI that is being used. The insert weighs between 50 and 100 pounds, and so a scanner movement system 15 is required to lift the insert 11 and place it on the MRI patient bed 16. The BrainPET workstation and fiber connection to the workstation are not shown.

As discussed above, the BrainPET insert is quite heavy, and as such in some embodiments, there is provided a lifting mechanism which may include mechanical assistance, for example, in the form of a hand-cranked lever or other similar method.

In FIG. 2 is a drawing showing the BrainPET Scanner 11 extended into the MRI bore 13. This figure shows the cart 12 at the back of the MRI 13, with the copper cable 14 extending into the MRI bore. The cable management tray 25 is used to hold the cable when it is not extended into the MRI bore. When the copper cable is inside the MRI, the cable management tray may be folded into the cart or may remain extended from the cart, depending on the details of the design.

The copper cabling between the insert and the cart needs to be managed using a suitable cable management system, some of which are known in the art. The cable management method that is used depends on whether the cable is flat, ribbon, round or some other cross-sectional shape.

In some embodiments, the cable will be about 16' long and may be tied up into a cable management method, for example, using echain or similar methods.

Figure 3:
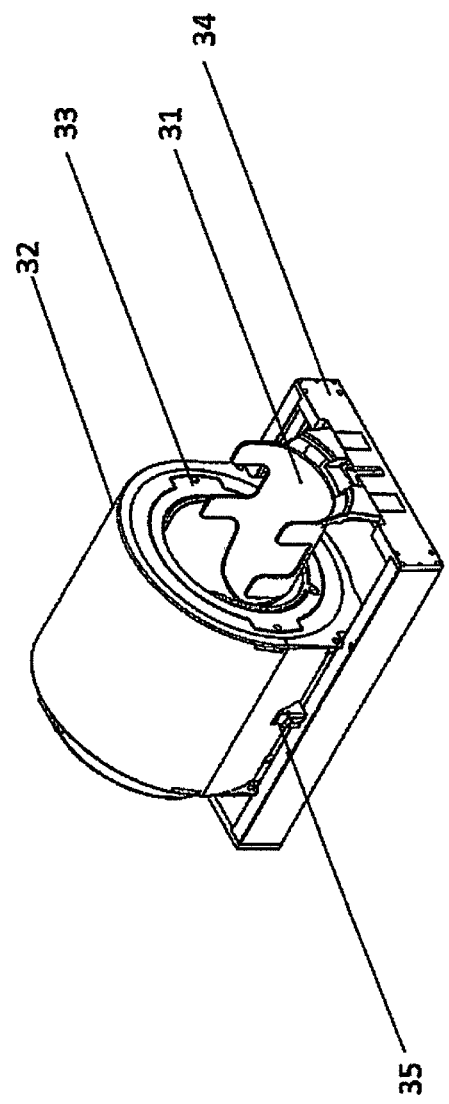
FIG. 3. BrainPET Insert rendering showing Head Holder, PET Ring, Tx coil, and Rx coil (red). Specifically, the Rx coil is at the inner-most position within the insert; the Tx coil is outside of and adjacent to the Rx coil and both the Rx coil and the Tx coil are within the PET ring.

The BrainPET insert is required for brain imaging, and the field of view will therefore be approximately 200 mm in axial extant and 240 mm in trans-axial. In some embodiments, the insert is made up of the elements:
1. PET Ring
2. Tx/Rx Coil
3. Headholder
4. Sliding System
5. Mattress for the patient head when placed in the headholder In FIG. 3 is shown the BrainPET Insert showing Head Holder (31), PET Ring (32), Tx/Rx coil (33). The PET Ring 32 and Tx/Rx coil are connected together into a single moveable unit, and they slide forwards and back on the Slide Platform 34. There are two locking positions for the PET Ring 32 and Tx/Rx coil, with the back or front position both being locked in place using the locks 35 on the side of the PET Ring. Only one lock is shown in this view. The Rx coil is at the inner-most position within the insert; the Tx coil is outside of and adjacent to the Rx coil and both the Rx coil and the Tx coil are within the PET ring.

As discussed above, the copper cable extends between the BrainPET insert and cart comprises one type of cable for the slow signals and a different type of cable for the fast signals, thereby preserving the important elements of the signal. As discussed above, the fast signals are used for timing, and so a sharp voltage edge is required and the sharp voltage edge of the timing signals can be input to a comparator circuit which digitizes the signal, as discussed above. For the slow signals, the voltages are used to generate a corner voltage value and an energy value, and a smoothed and monotonic amplitude measurement is required.

In some embodiments, the positioning of the patient into the MRI bore may be accurately determined by using the existing Siemens Biograph mMR laser positioning system and a marked location on the BrainPET system. In one embodiment, the marked location on the BrainPET system is exactly 138.8 mm from the front of the BrainPET. As a result of this arrangement, the Siemens bed system will move the patient into the correct part of the MRI once the button is pressed.

FIG. 9 shows a side view schematic drawing showing the patient's head 41 positioned on the headholder 31, with the BrainPET scanner 11 not fully over the patient head. The BrainPET Scanner 11 consists of PET Ring 32, inside of which is the Tx coil 45, inside of which is the Rx coil 46. Inside the PET ring are positioned the 4 scintillator blocks 47. The axial positioning of these scintillator blocks identify the PET Center of the field of view 48. The design of the system allows the PET isocenter to be positioned in line with the MRI isocenter. One method of aligning these two isocenters is to place a mark on the outside top of the PET Ring, and then using the Siemens alignment laser to accurately mark and move the patient to the middle of the MRI bore.

In some embodiments, the BrainPET is loaded onto the bed at the back of the MRI, and for horizontal alignment the triangular tabs on the back of the bed are used for properly aligning the BrainPET along the x axis, that is, across the bore.

Prior to imaging of the patient, the retractable PET Ring and Tx and Rx coil system can be moved back to allow the patient to place their head in the headholder. Once the patient is in place, the BrainPET can be moved to the front or imaging position which accurately positions the eye pieces of the coil over the eye locations of the patient and in some embodiments locked into place.

Accordingly, for use, as discussed herein, the PET ring 32 and the Tx/Rx coil 33 are positioned around the patient's head. In some embodiments, the PET ring 32 and the Tx/Rx coil 33 are approximately 200 mm in length. As discussed above, the slide platform 34 allows the PET Ring 32 to move back and forth. In some embodiments, the slide platform 34 is approximately 400 mm in length. The headholder 31 holds the patient's head. In some embodiments, the headholder 31 is attached to the front of the slide platform 34 and is approximately 200 mm in length).

For use, the PET ring 32 and Tx/Rx coil 33 can be located in 2 positions on the slide platform 34—either in the back position which exposes the headholder 31, or in the front position in which the headholder 31 is inside the PET ring 32 and Tx/Rx coil 33. In the back position, the headholder 31 is totally out of the PET Ring 32. In the front position, the headholder 31 is fully in the PET Ring 32.

The system is designed with the front and back positions so that the patient can easily put their head onto the headholder 31. When the patient sits on the patient bed and begins to lie down, the PET ring 32 and Tx/Rx coil 33 are in the back position so that they are out of the way of the patient. Once the patient's head is properly positioned on the headholder 31, the nurse slides the PET ring 32 and Tx/Rx coil 33 forward to the front position, which allows imaging of the patient's head.

In some embodiments, the MRI patient bed 16 slides on rails that are built into the MRI machine and has three positions.

In one embodiment of the invention, the workflow for the simultaneous MRI and PET scanning of a patient comprises the following steps:

Step 1—When the BrainPET docking station and scanner are first rolled into the MRI imaging room, they are rolled around to the back of the MRI system to allow the scanner to be positioned on the patient bed;

Step 2—Extend the patient bed out of the back of the MRI by a distance of approximately 75 cm. This distance will be different for different MRI systems;

Step 3—position the scanner on the patient bed;

Step 4—move the patient bed and scanner to the front of the magnet;

Step 5—nurse makes sure that the scanner is in the back position, exposing the headholder to allow for easy patient positioning;

Step 6—patient is positioned on the patient bed, with head in headholder. Patient positioning may include placing foam or supports around the head to ensure minimal head movement during MRI imaging;

Step 7—nurse moves scanner to the front position, with PET ring and MRI coil over top of the patient head;

Step 8—patient bed moves into the middle of the MRI to allow MRI imaging and PET imaging to occur. This scanning can take 20 to 30 minutes or more; and Step 9—patient bed moves to the front of the MRI and nurse moves scanner to back position, to allow patient to get off the bed.

While the preferred embodiments of the invention have been described above, it will be recognized and understood that various modifications may be made therein, and the appended claims are intended to cover all such modifications which may fall within the spirit and scope of the invention.

The invention claimed is:

1. A method of simultaneous PET and MRI Imaging of a patient's brain in an MRI system comprising a front, a back, a bore, a control system and a patient bed, said method comprising:

providing a BrainPET insert comprising, in order, a receive (Rx) coil positioned within and adjacent to a transmit (Tx) coil and a PET ring, wherein both the Rx col and the Tx col are within the PET ring, said patient bad comprising a sliding system extending from a position outside of the bore to a position within the bore, said sliding system moving the BrainPET insert from a first position wherein the BrainPET insert is mounted on the sliding system outside of the bore and a second position wherein the BrainPET insert Is within the bore;

moving the patient bed out of the back of the MRI device, thereby exposing a loading portion of the patient bed;

mounting the BrainPET Insert onto the loading portion of the patient bed such that the BrainPET insert is mounted on the sliding system and in the first position;

moving the patient bed out of the front of the MRI device for patient loading;

loading a patient onto the patient bed;

moving the patient bed such that the patient is moved into the bore;

moving the BrainPET insert from the first position to the second position such that the BrainPET insert is positioned around the head of the patient; and generating MRI and PET scans of the brain of the patient.

2. The method according to claim 1, wherein the patient places their head on a head holder.

3. The method according to claim 1, wherein the Rx coil and the Tx coil are removable from the BrainPET Insert.

4. The method according to claim 1, wherein the BrainPET insert comprises wheels and the sliding system comprises rails for moving the BrainPET Insert between the first position and the second position.

5. The method according to claim 1, wherein the PET ring is connected by a copper cable to the control system.

6. The method according to claim 5, wherein the copper cable comprises a fast signal cable and a slow signal cable.

7. The method according to claim 6, wherein the fast signal cable measures timing outputs.

8. The method according to claim 7, wherein the fast signal cable terminates at a comparator circuit for providing digital output of the timing outputs to the control unit.

9. The method according to claim 6, wherein the slow signal cable measures energy outputs.

10. The method according to claim 1, wherein the patient table is extended out the back of the MRI.

11. The method according to claim 1, wherein the sliding system includes locking means for securing the BrainPET insert in one or more specific positions.

12. A BrainPET Insert comprising, in order, a receive (Rx) coil positioned within and adjacent to a transmit (Tx) coil and a PET ring, wherein both the Rx coil and the Tx col are within the PET ring and are removable from the BrainPET insert.

* * * * *